(12) United States Patent
Irwin et al.

(10) Patent No.: US 8,936,634 B2
(45) Date of Patent: Jan. 20, 2015

(54) SELF CONSTRAINING RADIALLY EXPANDABLE MEDICAL DEVICES

(75) Inventors: Craig W. Irwin, Parks, AZ (US); James D. Silverman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 171 days.

(21) Appl. No.: 13/009,707

(22) Filed: Jan. 19, 2011

(65) Prior Publication Data

US 2011/0166637 A1  Jul. 7, 2011

Related U.S. Application Data

(63) Continuation-in-part of application No. 12/503,785, filed on Jul. 15, 2009, now Pat. No. 8,435,282.

(51) Int. Cl.
  *A61F 2/88* (2006.01)
  *A61F 2/90* (2013.01)
  *A61M 25/00* (2006.01)

(52) U.S. Cl.
  CPC ... *A61F 2/88* (2013.01); *A61F 2/90* (2013.01); *A61M 2025/0024* (2013.01)
  USPC ........................................ 623/1.15; 606/108

(58) Field of Classification Search
  CPC ............... A61F 2/88; A61F 2/82; A61F 2/90; A61M 2025/0024
  USPC ............. 623/11.11–1.13, 1.15, 1.11; 606/108
  See application file for complete search history.

(56) References Cited

U.S. PATENT DOCUMENTS

| | | |
|---|---|---|
| 3,225,129 A | 12/1965 | Taylor et al. |
| 4,141,364 A | 2/1979 | Schultze |
| 4,411,655 A | 10/1983 | Schreck |
| 4,569,347 A | 2/1986 | Frisbie |
| 4,601,713 A | 7/1986 | Fuqua |
| 4,655,771 A | 4/1987 | Wallsten |
| 4,732,152 A | 3/1988 | Wallsten et al. |
| 4,738,666 A | 4/1988 | Fuqua |
| 4,848,343 A | 7/1989 | Wallsten et al. |
| 4,875,480 A | 10/1989 | Imbert |
| 4,921,479 A | 5/1990 | Grayzel |
| 5,066,298 A | 11/1991 | Hess |
| 5,139,511 A | 8/1992 | Gill et al. |
| 5,171,262 A | 12/1992 | MacGregor |
| 5,171,305 A | 12/1992 | Schickling et al. |
| 5,176,659 A | 1/1993 | Mancini |
| 5,211,654 A | 5/1993 | Kaltenbach |
| 5,234,425 A | 8/1993 | Fogarty et al. |
| 5,318,588 A | 6/1994 | Horzewski et al. |
| 5,328,469 A | 7/1994 | Coletti |

(Continued)

FOREIGN PATENT DOCUMENTS

| | | |
|---|---|---|
| EP | 0 163 525 | 4/1985 |
| EP | 0682922 | 4/1994 |

(Continued)

*Primary Examiner* — Victor Nguyen
(74) *Attorney, Agent, or Firm* — David J. Johns

(57) ABSTRACT

The current invention discloses tubes that can be constrained and expanded by either axial or torsional strain. By torsionally displacing the tube in a direction counter to the biased helices and angularly displacing the lower angle helix to an angle equal to, but opposite, the starting angle, the tube is expanded diametrically with no significant change in length after expansion of the tube. These tubes find utility in medical and non medical applications.

14 Claims, 11 Drawing Sheets

(56) References Cited

U.S. PATENT DOCUMENTS

| | | |
|---|---|---|
| 5,352,236 A | 10/1994 | Jung |
| 5,364,345 A | 11/1994 | Lowery et al. |
| 5,382,399 A | 1/1995 | Moret de Rocheprise et al. |
| 5,395,349 A | 3/1995 | Quiachon et al. |
| 5,405,377 A | 4/1995 | Cragg |
| 5,445,646 A | 8/1995 | Euteneuer et al. |
| 5,447,503 A | 9/1995 | Miller |
| 5,458,573 A | 10/1995 | Summers |
| 5,464,419 A | 11/1995 | Glastra |
| 5,476,508 A | 12/1995 | Amstrup |
| 5,571,135 A | 11/1996 | Fraser et al. |
| 5,641,373 A | 6/1997 | Shannon et al. |
| 5,653,697 A | 8/1997 | Quiachon et al. |
| 5,662,703 A | 9/1997 | Yurek et al. |
| 5,690,644 A | 11/1997 | Yurek et al. |
| 5,762,604 A | 6/1998 | Kieturakis |
| 5,789,047 A | 8/1998 | Sasaki et al. |
| 5,800,456 A | 9/1998 | Maeda et al. |
| 5,824,041 A | 10/1998 | Lenker et al. |
| 5,833,699 A | 11/1998 | Chuter |
| 5,868,707 A | 2/1999 | Williams et al. |
| 5,893,868 A | 4/1999 | Hanson et al. |
| 5,993,427 A | 11/1999 | Rolland et al. |
| 5,997,508 A | 12/1999 | Lunn et al. |
| 6,025,044 A | 2/2000 | Campbell et al. |
| 6,039,721 A | 3/2000 | Johnson et al. |
| 6,042,605 A | 3/2000 | Martin et al. |
| 6,059,813 A | 5/2000 | Vrba et al. |
| 6,110,146 A | 8/2000 | Berthiaume et al. |
| 6,126,685 A | 10/2000 | Lenker et al. |
| 6,174,328 B1 | 1/2001 | Cragg |
| 6,238,410 B1 | 5/2001 | Vrba et al. |
| 6,254,628 B1 | 7/2001 | Wallace et al. |
| 6,280,412 B1 | 8/2001 | Pederson et al. |
| 6,352,561 B1 | 3/2002 | Leopold et al. |
| 6,371,980 B1 | 4/2002 | Rudakov et al. |
| 6,387,118 B1 | 5/2002 | Hanson |
| 6,432,130 B1 | 8/2002 | Hanson |
| 6,447,540 B1 | 9/2002 | Fontaine et al. |
| 6,468,243 B1 | 10/2002 | Miyagawa et al. |
| 6,544,278 B1 | 4/2003 | Vrba et al. |
| 7,105,013 B2 | 9/2006 | Durcan |
| 7,534,250 B2 * | 5/2009 | Schaeffer et al. ............. 606/191 |
| 7,625,337 B2 | 12/2009 | Campbell et al. |
| 7,766,820 B2 | 8/2010 | Core |
| 7,780,630 B2 | 8/2010 | Jenson et al. |
| 7,780,692 B2 | 8/2010 | Nance et al. |
| 8,435,282 B2 | 5/2013 | Silverman |
| 2002/0016607 A1 | 2/2002 | Bonadio et al. |
| 2002/0099431 A1 | 7/2002 | Armstrong et al. |
| 2002/0116045 A1 | 8/2002 | Eidenschink |
| 2003/0088309 A1 | 5/2003 | Iwasaka et al. |
| 2003/0176909 A1 | 9/2003 | Kusleika |
| 2003/0208223 A1 | 11/2003 | Kleiner |
| 2004/0044359 A1 | 3/2004 | Renati et al. |
| 2004/0087968 A1 | 5/2004 | Core |
| 2004/0143272 A1 | 7/2004 | Cully et al. |
| 2004/0143315 A1 | 7/2004 | Bruun et al. |
| 2005/0222576 A1 | 10/2005 | Kick et al. |
| 2005/0228479 A1 | 10/2005 | Pavcnik et al. |
| 2005/0245892 A1 | 11/2005 | Elkins et al. |
| 2005/0246008 A1 * | 11/2005 | Hogendijk et al. ......... 623/1.11 |
| 2005/0267568 A1 | 12/2005 | Berez et al. |
| 2006/0025844 A1 | 2/2006 | Majercak et al. |
| 2006/0030923 A1 | 2/2006 | Gunderson |
| 2006/0041302 A1 | 2/2006 | Malewicz |
| 2006/0074476 A1 | 4/2006 | Holman et al. |
| 2006/0155357 A1 | 7/2006 | Melsheimer |
| 2006/0184225 A1 | 8/2006 | Pryor |
| 2006/0184226 A1 | 8/2006 | Austin |
| 2006/0200221 A1 | 9/2006 | Malewicz |
| 2006/0276872 A1 | 12/2006 | Arbefeuille et al. |
| 2006/0282152 A1 | 12/2006 | Beyerlein et al. |
| 2006/0287671 A1 | 12/2006 | Renati et al. |
| 2007/0055338 A1 | 3/2007 | Dorn |
| 2007/0198077 A1 | 8/2007 | Cully et al. |
| 2008/0097301 A1 | 4/2008 | Alpini et al. |
| 2008/0312733 A1 | 12/2008 | Jordan |
| 2011/0144739 A1 | 6/2011 | Cattaneo |

FOREIGN PATENT DOCUMENTS

| | | |
|---|---|---|
| WO | 97/02791 | 1/1997 |
| WO | 98/33454 | 8/1998 |
| WO | 00/74584 | 12/2000 |
| WO | 02/38084 | 5/2002 |
| WO | 03/045284 | 6/2003 |
| WO | 2009/002827 | 12/2008 |
| WO | 2010/015370 | 2/2010 |
| WO | 2010/034453 | 4/2010 |

* cited by examiner

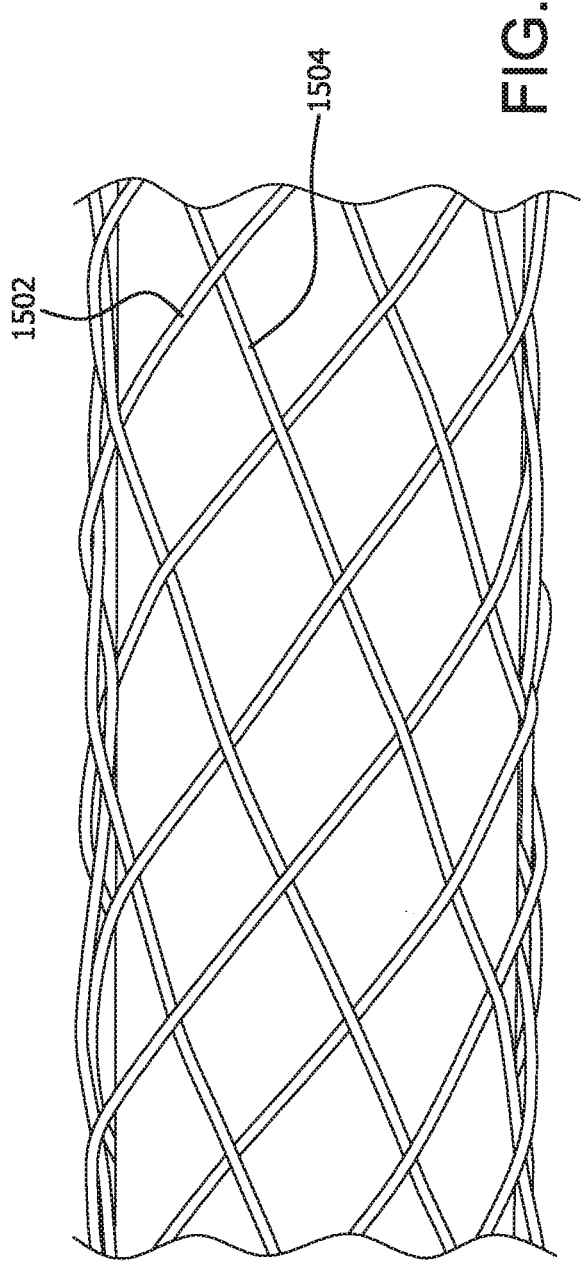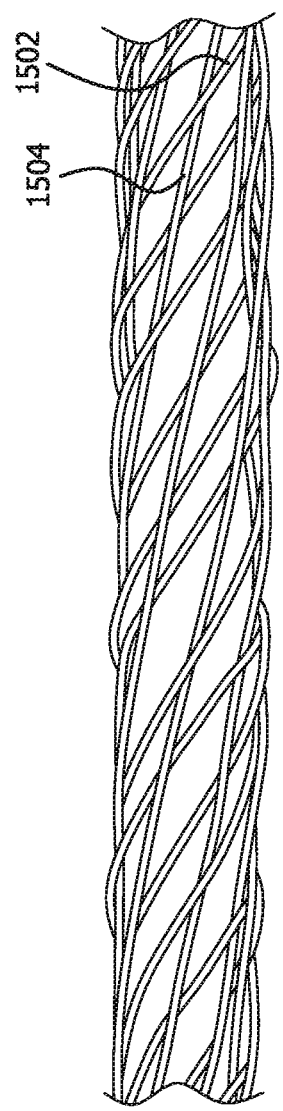
FIG. 15A
FIG. 15B

SELF CONSTRAINING RADIALLY EXPANDABLE MEDICAL DEVICES

CROSS REFERENCE TO RELATED APPLICATIONS

This application is continuation-in-part of U.S. patent application Ser. No. 12/503,785, filed Jul. 15, 2009 now U.S. Pat. No. 8,435,282, which is incorporated by reference herein.

BACKGROUND OF THE INVENTION

1. Field of the Invention

The present invention relates to an improved tubular structure with unique properties suitable for a wide array of applications, including use in manufacturing, as apparatus for positioning and deploying medical diagnostic and treatment devices in a body and in other uses.

2. Discussion of the Related Art

It is a known property of many tubular constructs, such as those made from flexible plastic materials, that the tube will contract in diameter if the tube is elongated longitudinally. This property is commonly referred to as "necking." Such necking can be problematic in many applications.

For instance, if a plastic wrap is applied over a mandrel in a manufacturing process, pulling on the end of the plastic wrap to remove the wrap from the mandrel will result in the wrap necking down on the mandrel. This often makes it difficult or impossible to slide the plastic wrap off the mandrel, requiring cutting of the wrap or distortion of the mandrel to separate the wrap.

Similarly, necking can likewise be a factor if a plastic tube is used to contain or constrain a device. For instance, in self-expanding medical devices for remote deployment in a patient, such as a stent or blood filter, the device designer must accommodate necking of the plastic tube if it is to be separated from the medical device through the relative sliding of the device and the constraining tube. Typically this requires using plastic tubes that resist necking, such as thicker and/or stiffer materials that can add undesirable profile to the device and/or reduce its flexibility and maneuverability within the body. Optimizing compactness and flexibility are highly desirable as physicians try to reach tighter treatment sites through smaller and more tortuous vessels.

Alternatively, a medical device designer may employ other deployment methods to separate the tube from the implantable device. For instance, a constraining sleeve can be designed to be cut or split from the implantable device, such as is described in U.S. Pat. No. 6,352,561 to Leopold et al. Others have suggested everting the sleeve to reduce the force required to slide the sleeve from the implantable device. Variations on this concept are described in, for instance, U.S. Pat. No. 4,732,152 to Wallsten, U.S. Pat. No. 5,571,135 to Fraser et al., U.S. Pat. No. 6,942,682 to Vrba et al., US Application 2006/0025844 to Majercak et al., and US Patent Application 2006/0030923 to Gunderson.

While everting sheaths can reduce the tension that must be applied to the constraining sleeve, they still can require considerable tension in order to pull the sheath over itself and the self-expanding device during deployment, resulting mainly from the friction of everted portion of the sheath rubbing against the non-everted portion of the sheath while the sheath is being removed. To whatever degree the sleeve material necks down on the device during deployment, this further complicates device design. These concerns are compounded with longer device lengths and more tightly compacted self-expanding devices that exert greater outward pressures. The greater the tension needed to evert and remove the sheath, the more demanding it is for the medical staff to remove the sheath while trying to hold the apparatus in its exact position during deployment. Increased deployment tensions also require more substantial sheath constructions so as to avoid sheath and deployment line breakage during deployment. It is believed that these deficiencies of everting sheaths may have limited practical applications for such deployment methods.

In co-pending U.S. Application Publication 2009/0182411 (Ser. No. 12/014,536 to Irwin et al.) a deployment sheath has been proposed that includes diametrically stored material to assist in sheath removal during implantable device deployment. For example, by constructing a constraining sheath with one or more folds or "pleats," it is much easier to evert the sleeve over itself during deployment by allowing the pleats to open as the sheath everts over itself. This essentially produces an inverse effect from necking—as the pleats open, the tubular sheath appears to grow diametrically while it is everting on itself. It has been found that this greatly aids in the deployment process. As a result, such pleated deployment sheaths are believed to be useful in a wide array of medical diagnostic and treatment devices, including stents, stent-grafts, balloons, blood filters, occluders, probes, valves, electronic leads, orthopedic devices, etc.

Plainly pleated tubes can be used not only to address the problem of necking, but actually can allow the tube to increase in effective diameter as axial force is applied to the tube. This is a major advancement over prior medical device deployment apparatus. Nevertheless, providing pleated sheaths with tightly controlled "growth" properties, as is required for medical device deployment, requires careful design and quality assurance controls. Pleated sheaths also work best when deployed in everted tube configurations.

Employing a pleated sheath to constrain and deploy a medical device such as when used as described above, may be desirable but it is recognized that a single layer of material would be preferable for such applications since it further reduces device profile.

Accordingly, it would be desirable to develop a tubular apparatus that is capable of increasing diametrically as axial tension is applied to it.

It would be further desirable to develop such a tubular construct that increases in diameter when axially elongated that can be used in single or multiple layers, both with and without pleats.

In addition, some stent or stent-graft designs include biased helical frames that are sheath constrained and foreshorten during deployment, making accurate placement difficult. The most common method of deploying a stent or stent-graft, as described herein, involves a removable constraining sheath. Sheath removal is accomplished through application of an axial force that is transmitted through the length of the catheter. Disadvantages associated with sheath constraint and deployment, in general, include sheath removal forces that scale with device length, packing pressure, compounding forces due to buckling of axially stressed catheter elements, catheter strain and added profile to the sheath itself. Although some of these issues are addressed herein, there are still disadvantages to using sheaths, currently known in the art, for constraining and deploying stents and other devices.

SUMMARY OF THE INVENTION

The present invention is directed to an improved tubular structure that is adapted to increase in diameter when axial force is applied to the structure. This increase in diameter may be accomplished by constructing the tube from multiple layers of material that move relative to each other during axial elongation of the tube. The tube of the present invention can be used both to avoid problems in "necking" found in many prior tube devices, and to provide additional benefits that increases in diameter of the tube during axial elongation can provide. As such, the tube of the present invention may be useful as a manufacturing aid, as a deployment sheath (for example, to deliver medical devices), and in other applications that may benefit from easier tubular sheath removal.

In one embodiment of the present invention, the tubular structure comprises a first helical wrap at a first wrap angle and a second helical wrap at a second wrap angle, the tubular structure having a first diameter and a first axial length. When the tubular structure is increased from the first axial length to an elongated second axial length, the first diameter increases to an enlarged second diameter.

In a further embodiment of the present invention, the tubular structure has a longitudinal axis comprising a wrap of at least one tape at a first wrap angle of x, and a wrap of at least one tape at a second wrap angle of y, with both wraps being in the same relative direction. The two wrap angles x and y are both formed at an angle of 0 to 90 degrees relative to the axis of the tubular structure, angle x being an angle different from angle y, and x and y oriented at an acute included angle with respect to each other. When axial force is applied to the tubular structure, both angle x and angle y decrease relative to the longitudinal axis, and the acute included angle between x and y increases. Preferably one or both of the tapes is anisotropic, being relatively non-compliant in the direction of wrap. Constructed in this manner, when the tubular structure is increased from the first axial length to an elongated second axial length, the first diameter increases to an enlarged second diameter.

A further defined construct of the present invention comprises a tubular structure having a first axial length and a first diameter wherein under tension an off-axis strain is formed in the tubular structure. When tension is applied to the tubular structure, the tubular structure assumes a second elongated axial length and an enlarged second diameter.

Further defined, the present invention comprises a tubular device having a tubular structure with at least one helically-oriented element and a diameter. Application of axial force to the tubular device causes the helically-oriented element to at least partially unwind, increasing the diameter of the tubular device.

One of the advantages of the present invention is that it can be utilized as a single layer of uniform thickness. When used, for instance, to deploy medical devices, these properties are believed to provide important benefits over prior everted and/or pleated tubes. However, it should be appreciated that the present invention can be incorporated with either everted or pleated constructs (or both) to provide additional improved properties. In all these various iterations, the present invention provides the benefit of allowing delivery of a remotely deliverable medical device with smaller and more flexible profile, and deployment of the device with less tension and more accurate placement.

As a medical device deployment apparatus, the present invention may be used to deploy a wide variety of devices to diagnose and/or treat patients. Such devices may include stents, stent-grafts, balloons, blood filters, occluders, probes, valves, electronic leads (e.g., pacing or defibrillator leads), orthopedic devices, etc. The deployment apparatus of the present invention may be modified to address many different device delivery and deployment needs. For instance, the number of wraps, the wrap angles, the types of wrap materials, the use of slits or other biasing means, the use of pleats, the orientation of the pleats, the use of sheath eversion, etc., can be adjusted to allow devices to deploy in different manners. Additionally, the sheaths of the present invention can be mounted in a variety of ways on devices to accommodate different deployment requirements, such as allowing a device to deploy off a catheter hub-to-tip, or tip-to-hub, or from a mid-point of a device outward in both directions.

Another embodiment of the invention comprises devices that are self constraining, eliminating the need for a sheath. For example, a stent or a stent graft can be delivered at a smaller profile if the stent or stent graft can be constrained without using a sheath. Thus, the invention also comprises a tube that can be constrained and expanded by applying torsional strain. By torsionally straining the tube in a direction counter to the biased helices and angularly displacing the lower angle helix to an angle equal to, but opposite, the starting angle, the tube is expanded radially with no significant change in length after expansion of the tube.

Thus, another embodiment of the invention comprises a tubular structure having a longitudinal axis comprising a first element oriented at a first angle of θ and a second element oriented at a second angle of γ, wherein θ does not equal γ, θ and γ are formed at an angle of between about plus or minus (+/−) 90 degrees relative to the axis of the tubular structure, and wherein when a first length section of the tubular structure is displaced rotationally relative to a second length section of the tubular structure, both θ and γ change during said rotation relative to the longitudinal axis and produce a change in diameter of at least a portion of the tubular structure. In another embodiment, said tubular structure has about the same length before and after expansion. In another embodiment, at a given small diameter and a given large diameter the lengths are equal. In another embodiment, the length of said tubular structure changes between a given small diameter and a given large diameter. In another embodiment, the angle of γ before expansion and angle of γ after expansion is equal and opposite in sign. In another embodiment, said first and second elements comprise metal, polymer, biomaterials or combinations thereof.

Another embodiment of the invention comprises a tubular construct comprising a first helical element having a first pitch angle, a second helical element having a second pitch angle, said second helical element being attached in part to the first helical element, wherein when a portion of the tubular construct is rotated, the first pitch angle and the second pitch angle change relative to each other. In another embodiment, said tubular construct has about the same length before and after expansion. In another embodiment, said first and second elements comprise metal, polymer, biomaterials or combinations thereof.

In another embodiment of the invention, at least a segment of the tubular construct has a given diameter, and wherein when a portion of the tubular construct is rotated so as to change the first pitch angle and the second pitch angle relative to each other, the diameter of at least a segment of the tubular construct changes. In another embodiment, at least a segment of the tubular construct has a given longitudinal stiffness, and wherein when a portion of the tubular construct is rotated so as to change the first pitch angle and the second pitch angle relative to each other, the longitudinal stiffness of the at least a segment of the tubular construct changes. In another embodiment, at least a segment of the tubular construct has a given length, and wherein when a portion of the tubular construct is rotated so as to change the first pitch angle and the second pitch angle relative to each other, the length of the at least a segment of the tubular construct changes.

In other embodiments of the invention, said tubular structures are used for a wide variety of medical uses, such as medical stents, stent grafts, grafts, filters, biopsy tools, occluders, embolectomy devices, angioplasty devices, stent expansion devices, catheters, endoscopes, and drug delivery devices, among other applications.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 13A depicts a tube with a symmetric weave. This tube cannot evenly expand or collapse by rotating or torquing tube 1306. FIG. 13B depicts an asymmetric weave. The asymmetry of the weave allows the tube to be constrained and unconstrained by torquing and also maintains the same length of the tube in a constrained and unconstrained configuration.

FIGS. 15A and 15B are elevation views of nitinol braided tubes woven in an asymmetric pattern in an open and/or expanded tube and/or an unconstrained tube configuration (15A) and in a closed and/or constrained (15B) configuration.

DETAILED DESCRIPTION OF THE ILLUSTRATED EMBODIMENTS

Reference will now be made in detail to an embodiment of the present invention, example of which is illustrated in the accompanying drawings.

The present invention is directed to an improved tubular structure that is adapted to increase in diameter when axial force is applied to the structure. This increase in diameter is preferably accomplished by constructing the tube from multiple layers of material that move relative to each other during axial elongation of the tube.

In its simplest form, the tubular structure of the present invention comprises a first helical wrap at a first wrap angle and a second helical wrap at a second wrap angle, the tubular structure having a first diameter and a first axial length. When the tubular structure is increased from the first axial length to an elongated second axial length, the first diameter increases to an enlarged second diameter. This concept is best illustrated in the model shown in FIGS. 1 and 2.

Figure 1:
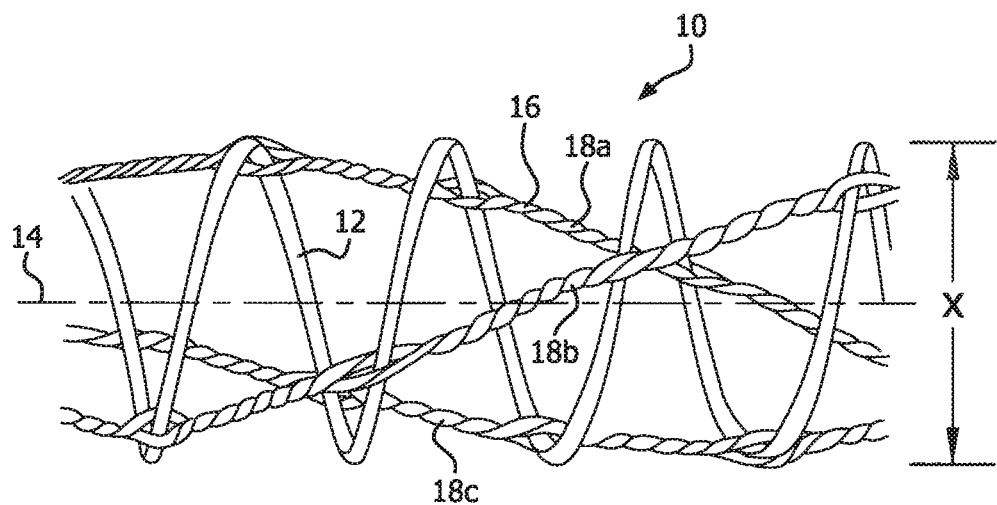
FIG. 1 is an elevation view of a schematic model demonstrating the concept of the present invention, in an unstrained configuration.

FIG. 1 shows a model 10 comprising a first helical structure 12, in the form of a permanently elongated SLINKY® spring toy, presenting a first wrap angle from axis 14. A wrap of a second helical structure 16, in the form of three strings 18a, 18b, 18c, is attached at approximately equidistant points around the first helical structure 12. In this first unstrained configuration the model comprises a first diameter x.

Figure 2:
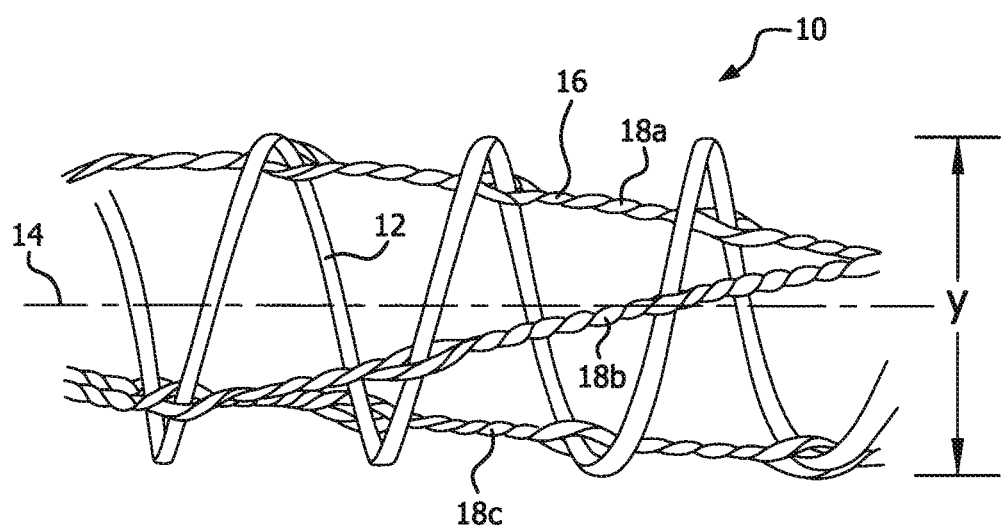
FIG. 2 is an elevation view of the schematic model of FIG. 1 with the model undergoing axial load, demonstrating an increase in the diameter of the model as the model elongates.

FIG. 2 shows the same model 10 with axial force applied to the structure, causing it to elongate. The effect of this elongation is that the angle of the second helical structure 16 reduces relative to the axis 14. This has the effect of essentially "untwisting" the first helical structure 12. This relative movement of the first helical structure causes the model 10 to grow radially to a second, enlarged diameter y. It will be appreciated that second helical structure 16 can be formed of any filament-like structure and does not require the three strings 18a, 18b, 18c as shown.

Figures 3, 4:
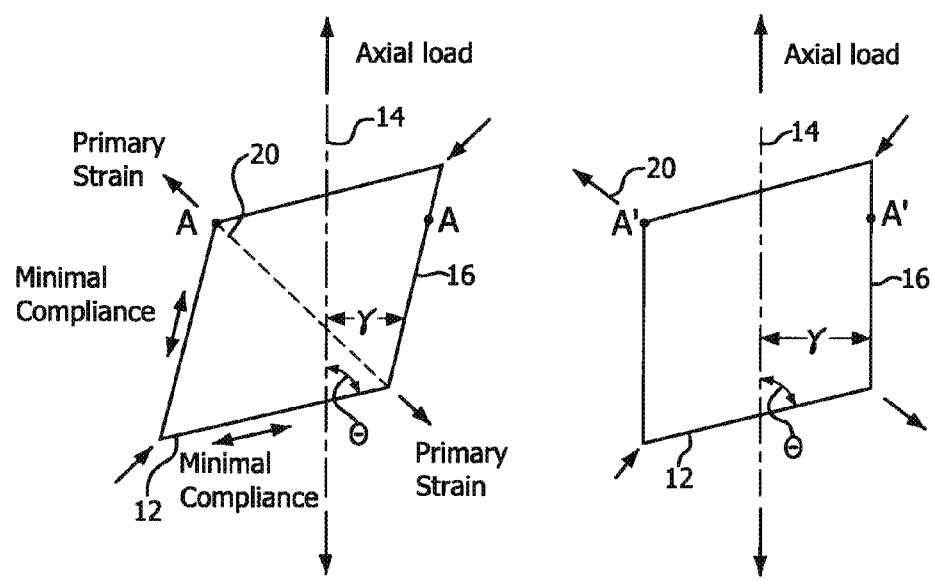
FIG. 3 is a diagram illustrating the relative orientations of the components of the present invention in a first, unstrained configuration.
FIG. 4 is a diagram illustrating the relative orientations of the components of the present invention in a second, strained configuration under an axial load.

This phenomenon may be further understood by reference to diagrams of FIGS. 3 and 4. FIG. 3 is a diagram illustrating in two dimensions a parallelogram element defining the relative orientations of the components of the present invention in a first, unstrained configuration. The axis of the tubular structure is defined by line 14. A first component 12 wrap angle is defined by angle Θ from axis 14. A second component 16 wrap angle is defined by angle γ from axis 14. As is noted in FIG. 3, it is desirable that the first and second components 12, 16 to have minimal compliance along their respective wrap angles Θ (high angle) and γ (low angle). Oriented in this manner, the direction of primary strain in this structure is along line 20. The circumference (diameter) of this tube is defined by the distance between points A-A.

When axial load is applied along line 14 to the structure of FIG. 3, the resulting reorientation of the structure is illustrated in FIG. 4. As the tube elongates, angle γ will decrease. The circumference as defined by line A'-A' will accordingly increase until angle γ eventually reaches zero (0).

By constructing a tube in this manner, it has been determined that tubes can be designed that can provide increases in diameter during elongation of 5, 10, 15, 20, 25% or more. Even greater diameter changes may be possible, with increases of 30, 35, 40, 45, 50% or more being readily achievable. Theoretically, even more substantial diameter changes of 100% to 500% to 1000% or more may be achieved, restricted by practical material and application limitations, such as true strain off of the oriented axis, wall thinning, axial lengthening, lack of oriented strength, etc. as the angles converge and approach the axis.

There are numerous options for creating a tube of the present invention. Preferably the tube comprises two or more unidirectional bias wraps of material at different angles around the intended axis. Preferably, the angle Θ of the first component is between about 0 and 90 degrees from the tube axis, with about 45 to 85 degrees being more preferred, and about 60 to 80 degrees being most preferable. Likewise, angle γ of the second component is between about 0 and 90 degrees from the tube axis, with about 10 to 80 degrees being more preferred, and about 20 to 60 degrees being most preferable. Overall, the small pitch, large wrap angle Θ component 12 provides hoop strength to the tube; the large pitch/small wrap angle γ component 16 provides axial strength and limits axial strain.

For some applications it may be desirable to include additional wraps of three, four, five, or more layers of material to provide additional strength, more thickness or cushioning, modified permeability, or other application-specific desirable properties.

The components of the tube of the present invention may take numerous forms. For most applications it is preferred to employ tapes of material that provided oriented strength and minimal compliance in the direction of their respective wrap angles. The first component should be fixed to the second component such that a change in angle of the first component produces a resulting change in angle of the second component relative to the longitudinal axis of the tube. Off of their wrap angles, for many applications it is preferable to have a more compliant material that will allow the orientation of the two active components to change relative to each other so as to provide maximum diameter growth during axial elongation. Suitable materials for use in the present invention may include, without limitation, fluoropolymers (especially polytetrafluoroethylene (PTFE) and fluorinated ethylene propylene (FEP)), polyethylenes, polyethylene teraphthalate (PET), nylon, polyurethane, polypropylene, polyester, polyimide, etc., as well as composite materials combining these and/or other materials to achieve the desired strength and compliance characteristics. Expanded PTFE (ePTFE) is believed to be most preferred for many applications since it provides excellent axial strength in the direction of expansion but is readily compliant in a direction perpendicular to the direction of expansion.

Depending on applications, tubes of the present invention may be constructed from a continuous material, such as continuous films, tapes, or sheets of materials. Alternatively, the inventive tubes may include discontinuous structures, such as sheets or tapes that include holes or slits therein, or even materials formed from weaves, knits, or other open structures.

Without intending to limit the scope of the present invention, FIGS. 5 through 8 illustrate various embodiments that may be useful to practice the present invention.

Figure 5:
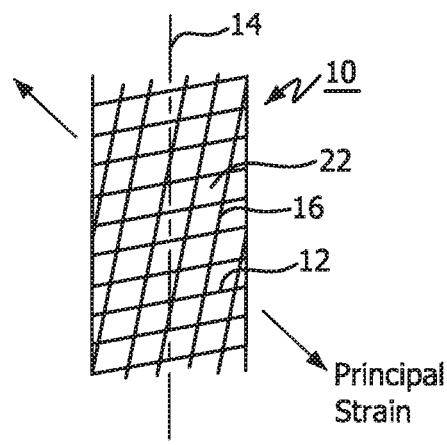
FIG. 5 is a schematic representation of a first embodiment of a tube of the present invention.

FIG. 5 illustrates an embodiment of the present invention that comprises a fully open mesh tube 10. In this embodiment first component 12 and second component 16 each comprises a fiber or wire material. Open spaces 22 are provided between the two components 12, 16 that can be left unfilled or can be covered with a layer of other material (for example, a continuous or discontinuous film). Suitable materials that may be used as one or the other or both of components 12, 16 may include metals such as steel, nitinol, etc., polymers such as nylon, ePTFE, etc. As has been noted, with the right selection of components 12, 16 and with spaces 22 left unencumbered, this construction is believed to provide optimal growth characteristics in accordance with the present invention.

Figure 6:
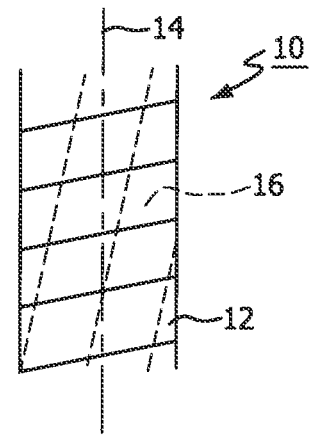
FIG. 6 is a schematic representation of a second embodiment of a tube of the present invention.

FIG. 6 illustrates an embodiment of a tube 10 of the present invention that comprises a biased wrapped tube of two film (or "tape") components 12, 16. Preferably the two tape components are uniaxially oriented materials with minimal shear and transverse strength. As has been discussed above, ePTFE is particularly desirable for use as one or both of these components.

Figure 7:
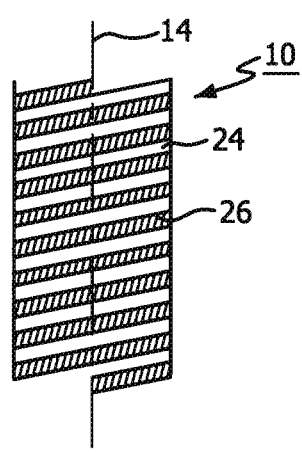
FIG. 7 is a schematic representation of a third embodiment of a tube of the present invention.

FIG. 7 illustrates yet another embodiment of a tube 10 of the present invention. This embodiment employs a fine pitch angle helix of full density, high modulus film 24, such as a polyimide, and a low angle pitch of uniaxial film 26, such as ePTFE.

Figure 8:
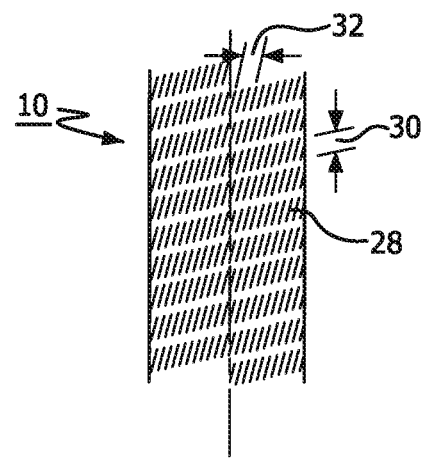
FIG. 8 is a schematic representation of the fourth embodiment of a tube of the present invention.

FIG. 8 illustrates still another embodiment of the present invention. In this embodiment the tube 10 comprises a homogenous material with both high and low angle orientations defined by oriented slits 28 in the homogenous material. Low angle component slits are oriented in helical rows 30 around the circumference of the tube, while high angle component slits are defined as diagonals lines 32 across the low angle rows 30.

The above examples are only a few of the many various orientations of the present invention that can be constructed. For example, it should be appreciated that many of the properties of the various embodiments of FIGS. 5 through 8 can be combined, such as constructing a tube with both the continuous material of FIG. 6 combined with selected open spaces of FIG. 5, or combining the high modulus film of FIG. 7 with any of the other three constructs, or employing oriented slits of FIG. 8 on part or all of any of the other three constructs, etc.

The tube of the present invention can be used both to avoid problems in "necking" found in many prior tube devices, and to provide additional benefits that increases in diameter of the tube during axial elongation can provide. As such, the tube of the present invention may be useful as a manufacturing aid, as a deployment sheath (for example, to deliver medical devices), and in other applications that may benefit from easier tubular sheath removal.

Figure 9:
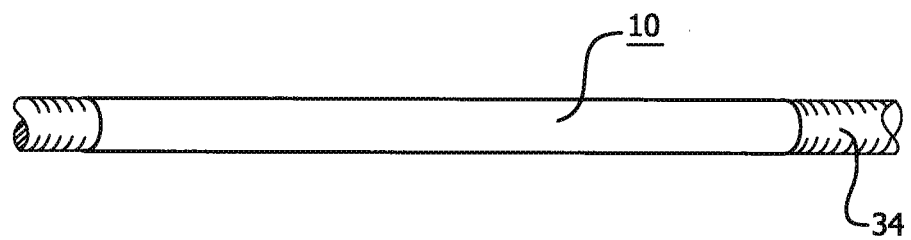
FIG. 9 is a plan view of a tube of the present invention mounted over a mandrel.

FIG. 9 illustrates one such application wherein the tube 10 is mounted on a manufacturing mandrel 34, such as those commonly employed to construct various tubular structures (e.g., taped-wrapped vascular graft components). Heating or other processing steps can shrink the tube around the mandrel, making it difficult or impossible to slide the tube off the mandrel once the manufactured article is removed. With the tube of the present invention, axial movement of the tube 10 causes it to diametrically grow, making its removal from the mandrel much easier. This property may also be highly beneficial in assisting in removing a manufactured article from a mandrel.

Figure 10:
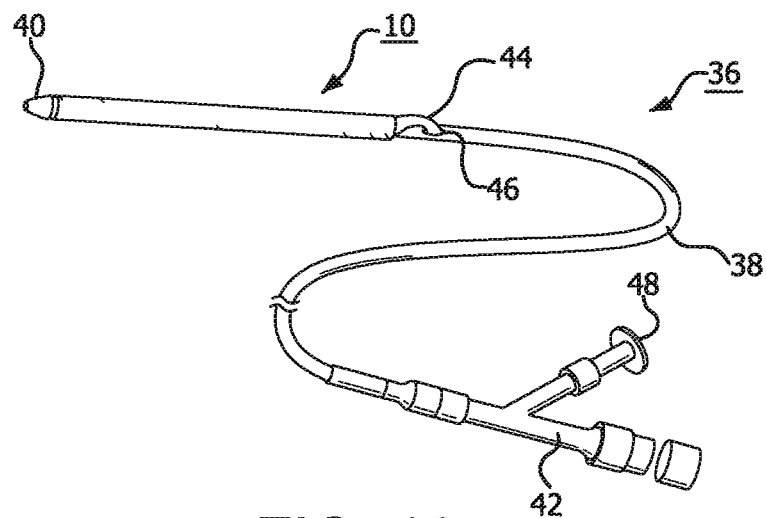
FIG. 10 is a plan view of an embodiment of a tube of the present invention employed in a medical device deployment system mounted near a distal end of a delivery catheter.

Shown in FIG. 10 is one embodiment of a tube 10 of the present invention mounted as a containment sheath near the end of a medical device deployment system 36. The deployment system comprises a catheter shaft 38 extending from a distal olive 40 to a control hub 42. A medical device, such as a stent, stent-graft, balloon, blood filter, occluder, probe, valves, etc. may be contained in the sheath 10 to be deployed at a treatment site within a patient's body. The sheath 10 may be everted over itself to form two layers, an exterior segment that partially or completely covers an interior segment. The tube 10 is attached to a deployment line 44 that is fed into the catheter shaft through opening 46. The deployment line 46 is operatively connected to a deployment knob 48 on the hub 42.

The tube 10 made in accordance with the present invention may be formed from any material that is sufficiently strong both to constrain the device to be delivered and to withstand the tension of the removal process. It is desirable that the sheath 10 also be as thin and lubricious as possible so as to maintain a small device delivery profile and to facilitate the removal process. Since the tube 10 is placed temporarily deep within a patient during delivery and deployment, it is likewise desirable that the sheath be formed from a biocompatible material. As is explained in greater detail below, suitable sheath materials may include: polytetrafluoroethylene (PTFE); expanded PTFE (ePTFE); fluorinated ethylene propylene (FEP), polyethylene teraphthalate (PET), nylon, polyurethane, polypropylene, polyester, etc.

In order to actuate the deployment line 44, medical personnel will unscrew the deployment knob 48 and pull on the knob and connected deployment line to cause the tube 10 to progressively withdraw off of the contained device. If the tube 10 is everted over itself, as the exterior segment of the tube is withdrawn, the tube of the present invention will progressively increase in diameter, steadily everting the interior segment so that it becomes the exterior segment of the tube. The diametrical growth of the tube 10 of the present invention aids in the process of everting, since the exterior segment of the tube 10 will form a larger diameter than the unstrained interior segment. As a result, the larger diameter exterior segment slides easily over the interior segment and is readily removed with minimal friction between the two layers.

Figure 11:
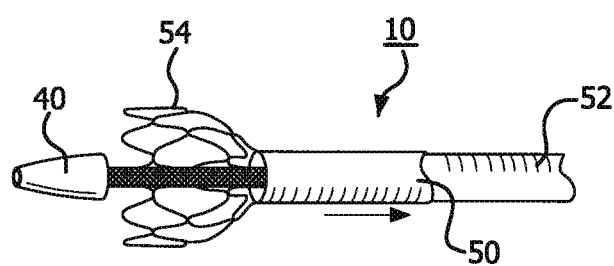
FIG. 11 is an enlarged perspective view of a distal end of a delivery catheter showing tube of the present invention being withdrawn, progressively releasing a self-expanding stent contained therein.

The process of device delivery can be better seen in FIG. 11. In this embodiment, an exterior segment 50 is shown withdrawing over an interior segment 52, shown exposed in cut-away. As the larger diameter exterior segment 50 is withdrawn, the axial force opens up the tube 10 of the present invention. As the tube 10 is withdrawn in this manner, a constrained self-expanding stent 54 is progressively deployed from this embodiment.

It should be appreciated that medical device deployment using the present invention may be accomplished as a single layer or in an everted manner as discussed above. When employing an everted embodiment, in the final construct the exterior segment should have an inner diameter that is sufficiently greater than the outer diameter of the interior segment in order to minimize friction between the two segments. That is, in order to minimize interference between the interior segment and the exterior segment, the axially elongated exterior segment should enlarge enough so that its inner diameter comfortably clears the outer diameter of the unstrained interior segment. It is preferred that the inner diameter of the exterior segment be 0.1 to 50% larger than the outer diameter of the interior segment, and more preferably 10 to 20% larger.

For example, to achieve these dimensions, a tube with a wall thickness of about 0.08 mm and an exterior segment inner diameter of about 2.1 mm will typically be provided with an unstrained interior segment having an outer diameter of about 1.9 mm.

The tube of the present invention is believed to vastly reduce the amount of tension required to deploy a device.

The advantages of the tube of the present invention are believed to be readily adaptable to improve many other devices and processes. One example of such improved combination is to employ the tube of the present invention with the pleated tube deployment constructs that are disclosed in co-pending U.S. Application Publication 2009/0182411 (Ser. No. 12/014,536 to Irwin et al.) filed Jan. 15, 2008, incorporated herein by reference. In this regard, the tube of the present invention can be used with one or more pleats to aid in device delivery and provide further beneficial results.

Another embodiment of the invention comprise devices that are self constraining, eliminating the need for a sheath. For example, a stent or a stent graft can be delivered at a smaller profile if the stent or stent graft can be constrained without using a sheath. Thus, the invention also comprises a tube that can be constrained and expanded torsionally. By torsionally displacing the tube in a direction counter to the biased helices and angularly displacing the lower angle helix to an angle equal to but opposite the starting angle, the tube is expanded radially with no resultant change in length after expansion of the tube. As depicted in FIGS. 12A and 12B and 15A and 15B, FIGS. 12A and 15B is a tube that is closed and/or constrained and FIGS. 12B and 15A depict an open and/or expanded tube and/or an unconstrained tube. In this embodiment, said tube is composed of filaments, however the same can be accomplished by using tape wrapped tubes.

Figure 12A:
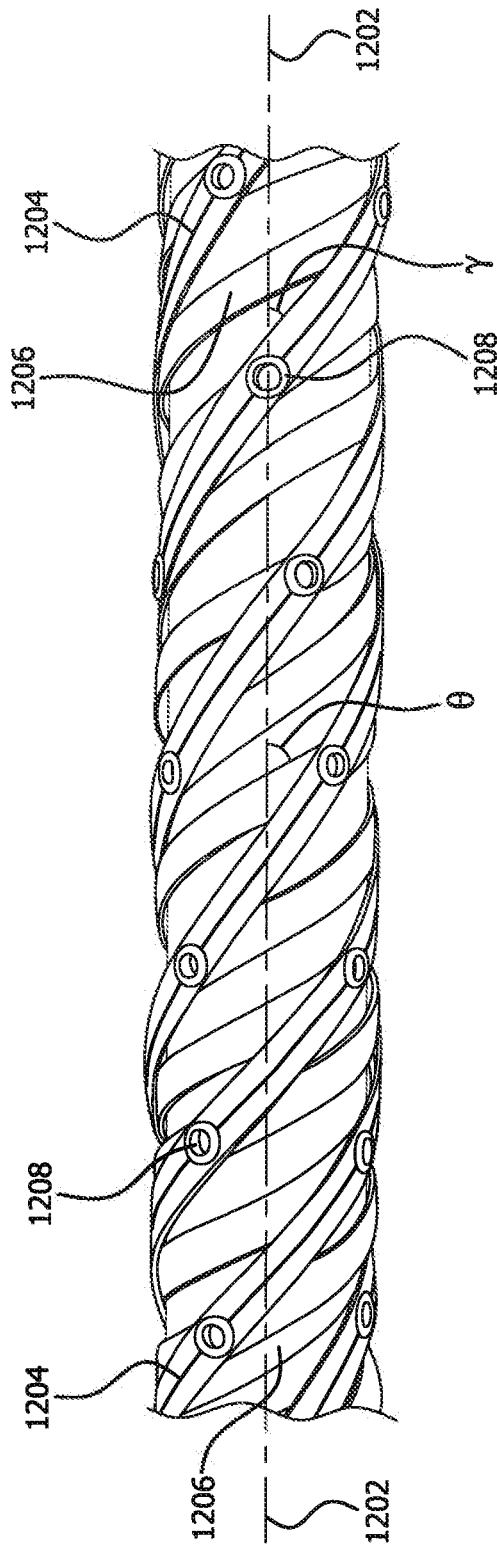
FIG. 12A is an elevation view of a collapsible tube that is closed and/or constrained and 12B depicts the same tube in an open and/or expanded tube and/or an unconstrained tube position. In this embodiment, said tube is composed of filaments.
Figure 12B:
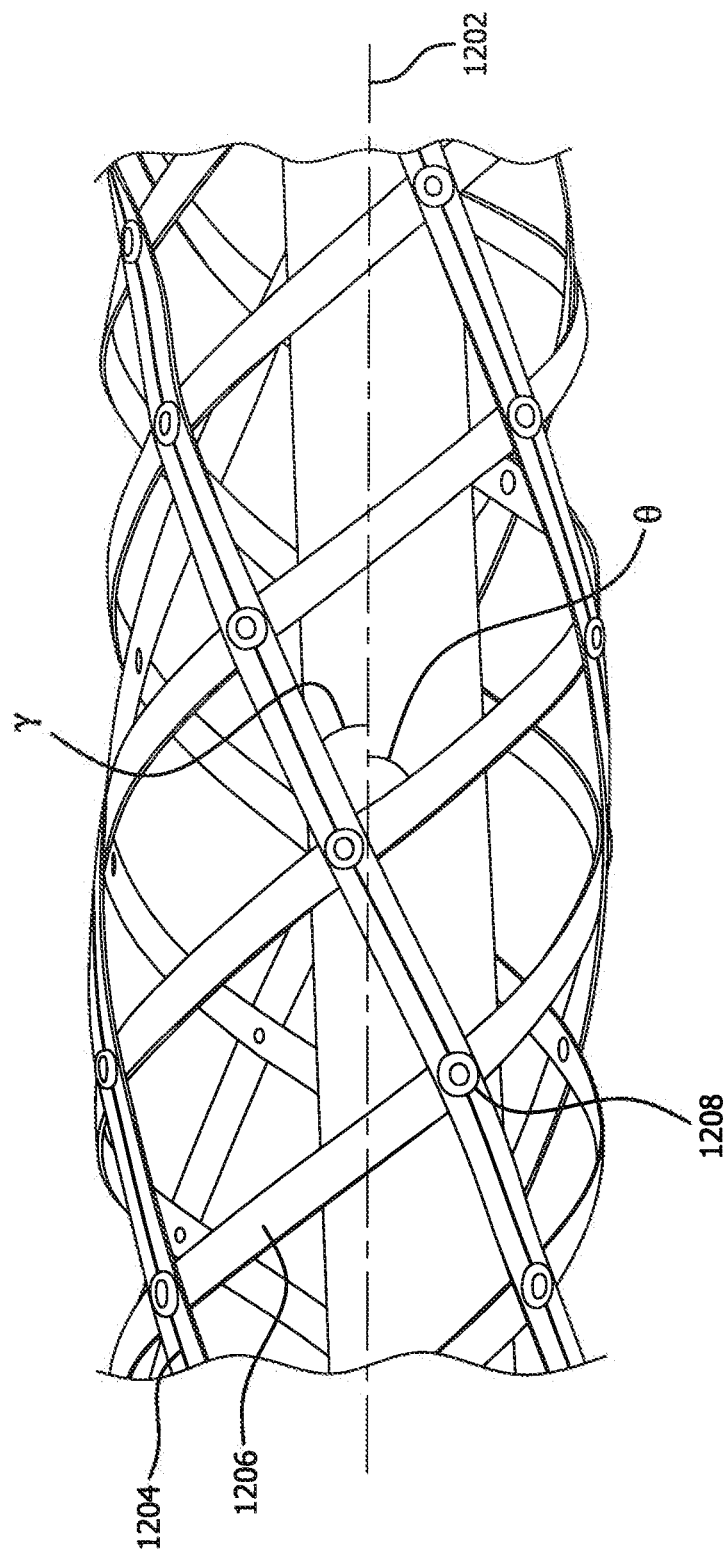

Referring to FIGS. 12A and 12B, one embodiment of the invention comprises a tubular structure comprising a longitudinal axis 1202 and a first element 1204 oriented at a first angle $\gamma$, relative to the longitudinal axis 1202. The tubular structure also comprises a second element 1206 oriented at a second angle $\theta$, relative to the longitudinal axis 1202. As shown in FIG. 12A the tube is constrained around a mandrel. When the tube is in an unconstrained configuration, as depicted in FIG. 12B, both $\theta$ and $\gamma$ change relative to the longitudinal axis and produces a change in diameter of at least a portion of the tubular structure. In one embodiment, $\theta$ does not equal $\gamma$ when constrained and unconstrained (asymmetric). During radial expansion of the tube, both angles will change, but both angles may not change from a given final constrained state to a given final unconstrained state and visa versa. In another embodiment, during radial expansion of the tube, $\theta$ will never equal $\gamma$. In another embodiment, $\theta$ and $\gamma$ are formed at an angle of between about +/−90 degrees relative to the axis 1202 of the tubular structure. In another embodiment, when the tubular structure is displaced rotationally, both $\theta$ and $\gamma$ change relative to the longitudinal axis 1202 and produce a change in diameter of at least a portion of the tubular structure. In another embodiment, said tubular structure has about the same length before and after expansion. In another embodiment, at a given small diameter and a given large diameter the length of the tubular structure remains about equal. In another embodiment, the length changes between a given small diameter and a given large diameter. In another embodiment, the angle of $\gamma$ before expansion and angle of $\gamma$ after expansion is equal and opposite in sign.

Figure 16:
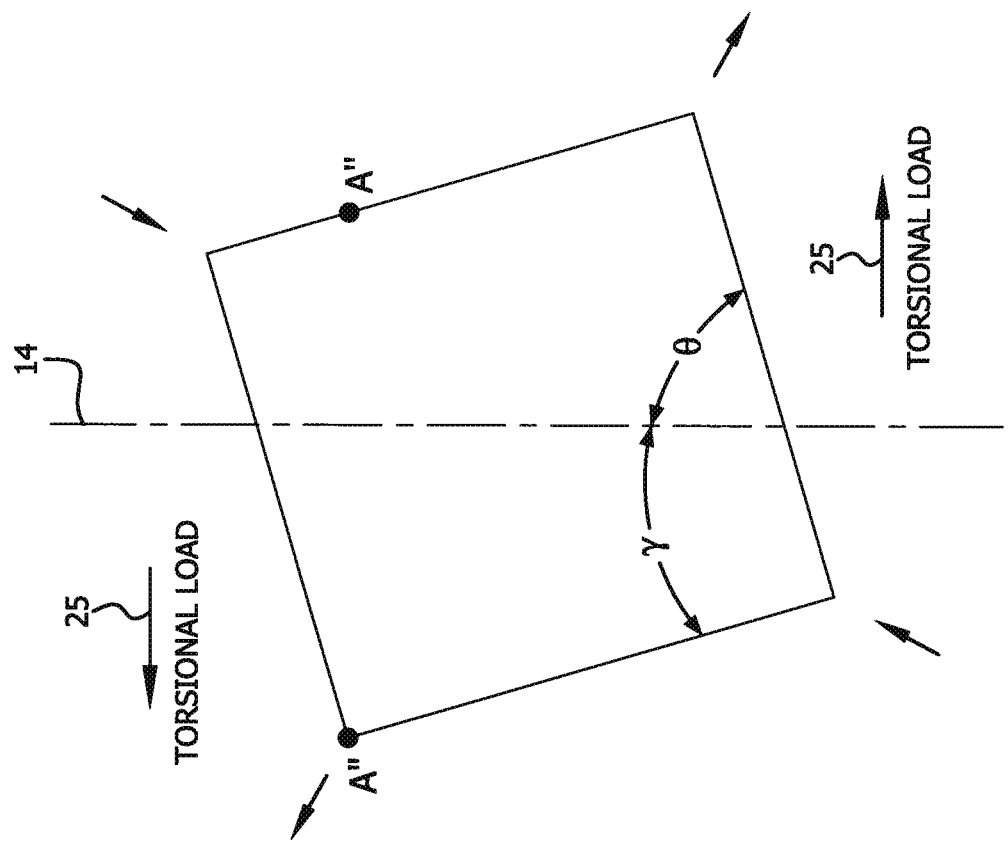
FIG. 16 is a diagram illustrating the relative orientations of the components of the present invention in a torsionally expanded configuration in which the helical direction of the low angle component has been reversed relative to FIG. 3.

This phenomenon may be further understood by reference to diagrams of FIGS. 3 and 16. FIG. 3 is a diagram illustrating in two dimensions a parallelogram element defining the relative orientations of the components of the present invention in an unstrained configuration. The axis of the tubular structure is defined by line 14. A first component 12 wrap angle is defined by angle $\Theta$ from axis 14. A second component 16 wrap angle is defined by angle $\gamma$ from axis 14. As is noted in FIG. 3, it is desirable that the first and second components 12, 16 to have minimal compliance along their respective wrap angles $\Theta$ and $\gamma$. Oriented in this manner, the direction of primary strain in this structure is along line 20. The circumference (diameter) of this tube is defined by the distance between points A-A. In FIG. 16 when a torsional displacement 25 is applied about axis of line 14 to the structure of FIG. 3, the resulting orientation of the structure is illustrated. In this embodiment, the low angle γ component is reversed in the helical direction increasing the circumference (diameter), as defined by line A″-A″. The circumference will continue to increase as γ continues to increase relative to axis 14.

In another embodiment of the invention, said first element and second element have an attachment point that allows the filament to pivot relative to each other, as depicted in FIG. 12A as pivot point 1208. Thus, another embodiment of the invention comprises, a tubular construct comprising a first helical element having a first pitch angle, a second helical element having a second pitch angle, said second helical element being attached in part to the first helical element, wherein when a portion of the tubular construct is rotated, the first pitch angle and the second pitch angle change relative to each other. In another embodiment, said tubular construct has about the same length before and after expansion. In another embodiment, said first and second elements comprise metal, polymer, biomaterials or combinations thereof. In another embodiment, said tubular structure is a stent. In another embodiment said stent further comprises a graft.

It will be appreciated that the tubular constructs of the invention, for example that are shown in FIGS. 12A and 12B, can be at least partially covered and/or lined. Said cover or liner may be solid, perforated, or comprised of filaments or "webs". Thus, another embodiment of the invention comprises a covered, asymmetrically wrapped tubular structure.

Another embodiment of the invention comprises at least a segment of the tubular construct that has a given diameter, and wherein when a portion of the tubular construct is rotated so as to change the first pitch angle and the second pitch angle relative to each other, the diameter of said segment of the tubular construct changes. In another embodiment, at least a segment of the tubular construct has a given longitudinal stiffness, and wherein when a portion of the tubular construct is rotated so as to change the first pitch angle and the second pitch angle relative to each other, the longitudinal stiffness of the at least a segment of the tubular construct changes. In another embodiment, at least a segment of the tubular construct has a given length, and wherein when a portion of the tubular construct is rotated so as to change the first pitch angle and the second pitch angle relative to each other, the length of the at least a segment of the tubular construct changes.

Figure 13A:
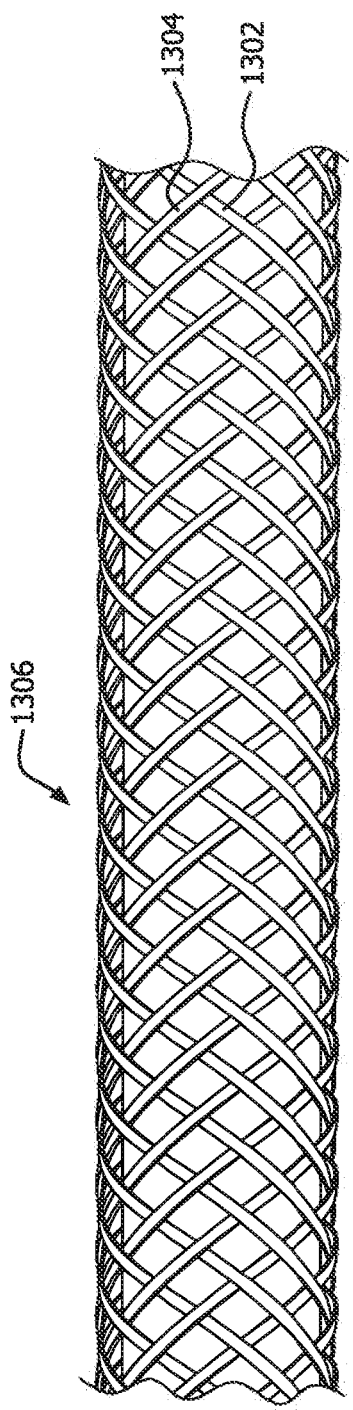
FIGS. 13A and 13B are elevation views of tubes made of filaments woven in a symmetric and asymmetric pattern.
Figure 13B:
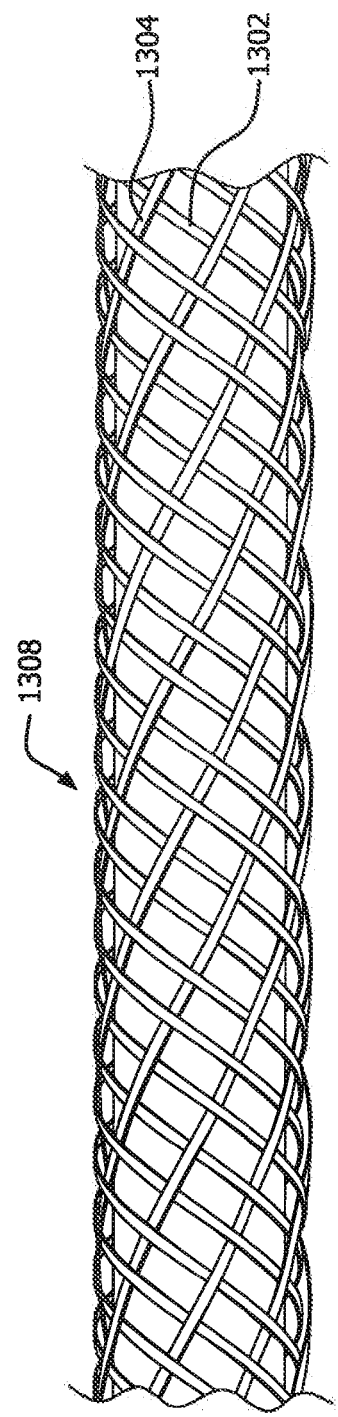

FIGS. 13A and 13B depict tubes made of filaments 1302 and 1304 woven in a symmetric and asymmetric pattern. FIG. 13A depicts a tube with a symmetric weave. This tube cannot be evenly collapsed by torquing tube 1306. FIG. 13B depicts an asymmetric weave. The asymmetry of the weave allows tube 1308 to be constrained and unconstrained by torquing and also maintains the length of the tube in its fully constrained and fully unconstrained configuration. For this example the asymmetric weave was created on a Steeger Braider (Steeger USA, Inman, S.C.). The asymmetric weave was made by rotating the mandrel on the take up to create the asymmetric construct.

Unique features of tubular constructs utilizing an asymmetric bias structure include: an ability to simultaneously increase or decrease in both radial and axial dimension; a defined relationship between radial dimension, axial dimension and torsional displacement; and pairs of conditions for a given structure in which diameters are different but axial length is substantially unchanged. Such tubes have utility in many applications. In one embodiment, the tube design has utility in applications where a tube or cavity needs to be expanded and/or held to a desired diameter or shape. One such embodiment comprises a stent which functions to widen or expand and holds open a tube (such as a vessel) or cavity. Said stent can be formed by weaving filaments in an asymmetric pattern to create a tube. The stent is self-constraining, i.e., torsionally constrained at a delivery profile, eliminating the need for a constraining member, e.g., a sheath. In the absence of the constraining member, the stent can be delivered at a smaller profile and does not require the application of an axial force for deployment. Instead, torsional forces may be employed for constraint and/or deployment and can be transmitted with greater efficiency than an axial force due to lower required forces and the absence of buckling. Thus, the invention also comprises a tube that can be expanded torsionally. By torsionally displacing the tube in a direction counter to the biased helices and angularly displacing the lower angle helix to an angle equal to, but opposite, the starting angle, the tube is expanded diametrically with no significant resultant change in length after expansion of the tube. The absence of length change (also referred to as "foreshortening") is a desirable quality in a stent. In another embodiment, the ends of the stent can be held in place by lock pins, hooks or other methods known in the art.

In addition, stent rings can be formed in an asymmetric pattern. Expansion of the stent rings comprising an asymmetric pattern also prevents foreshortening of the rings. Said asymmetric cut ring of can be cut from materials such as metals and polymers and can be cut by any method known in the art, e.g. laser cutting. Rings can be attached to each other by methods known in the art, including, but not limited to, methods described in U.S. Patent Application Publication 2009/0182413, incorporated by reference herein for all purposes.

In another embodiment, when said stent or stent ring is made from a polymer or any other material that has polymer based creep (memory) said stent can be expanded to overcome the memory. Because the expansion is via torquing, the effect of creep can be overcome. In another embodiment, a polymer containing stent, such as a drug eluting stent, can be torqued closed by a physician just before implantation and expanded in a vessel. This method prevents creep in a polymer containing stent during shipping and/or storage. In one embodiment, said stent is a bioabsorbable stent. In another embodiment, said bioabsorbable stent is comprised of a biomaterial such as collagen, a metal such as magnesium, or a polymer such as polyglycolic acid (PGA).

Because stents made in accordance with the invention can be expanded and also contracted via rotational force applied to them, said stents can also be placed by expansion and subsequently constricted, moved in location and then re-expanded. This offers the advantage of an easily re-positionable stent. In yet another embodiment, the stent, once expanded may be further expanded using a balloon expansion device as is known in the art.

In another embodiment the tubes of the invention may be made as variable diameter vascular grafts.

In another embodiment of the invention, pressure differentials applied to a surface of the tubes are used to create a change in diameter producing torsional displacement. When pressure is relieved, and assuming the tube is constructed to be elastic in its behavior, the tube may contract to its original (or close to its original) configuration/state. This feature of the invention may be used to remotely expand and contract the tube while also creating a rotational motion. One application is to configure the tube as a balloon which features rotational motion as it expands.

The asymmetrically wrapped tubes of the invention may also be configured to serve as catheter (or endoscope) centering and/or stabilization devices where said tube forms a part of a catheter. The tube is constrained about the catheter until the catheter is placed in a desired position within a lumen or cavity. The tube is then expanded axially away from the catheter body by the application of rotational motion and contacts the side of the lumen or cavity which in turn axially centers the catheter within the lumen or cavity. In another embodiment, the asymmetrically wrapped tubes of the invention may be configured to serve as anchors for devices such as catheters, stents and other indwelling devices. In such cases, the tube is configured as a part of the device to be anchored. The tube is kept constrained until the device to be anchored is properly positioned whereupon the tube is expanded by the application of torsional force and comes in contact with an anchoring surface, e.g., a vessel wall. Expansion of the tube at an appropriate force normal to the axis of the device maintains the device in position. Such anchoring function may be used in conjunction with anchoring of cardiac or neurostimulation lead tips, anchoring of sensors within body vessels and cavities, positioning and anchoring of treatment devices (e.g., ultrasound transducers) and the like.

In another embodiment of the invention, an asymmetrically wrapped tube of the invention, serving as a stent as detailed above may be reconstrained and removed from its deployment site. Removal may occur after relatively long periods of time as treatment might dictate or in the event of stent failure. Removal may occur after relatively short periods of time as well. Such "temporary stents" have application in the treatment of urological conditions such as prostatic obstruction, other stenotic conditions such as tracheal stenoses and during lytic treatments for stroke where the obstruction must be held open until lytic drugs have adequately dissolved the clot whereupon the temporary stent may be removed.

In another embodiment of the invention, an asymmetrically wrapped tube of the invention is configured to selectively block or occlude a lumen, cavity or opening once expanded. For example, the tube may be used for atrial septal defect repair of the mammalian heart or as an endovascular coil for aneurysm treatment.

Another embodiment of the invention is as an expandable and constrainable flange or grommet. An asymmetrically wrapped tube is constructed in an "hourglass" shape and then constrained into a smaller, more or less uniform diameter tube. The tube is passed through an opening with opposing ends remaining out of the opening and expanded. The ends of the tube expand more than the center and the tube reassumes its hourglass configuration, anchoring the tube on both sides of the opening. In certain embodiments the flange is solid; in others the flange is perforated to allow substances to pass through. For example, such a flange, constructed in accordance with the invention, can be used to create or modify a fistula, e.g., in a body vessel, create a catheter connector or stoma placed through the skin, or serve as attachment means for a vocal prosthesis. In many embodiments, the flange diameter is highly adjustable making it ideal for use in varying opening diameters.

In another embodiment of the invention, a construct of the present invention in a reduced diameter form may be positioned with a tube lumen or cavity and then expanded by rotational motion to mechanically widen (or clear an obstruction from) said lumen or cavity and then subsequently be re-constricted and removed. For example, an asymmetrically wrapped tube can be delivered to a site within an artery where atherosclerotic plaque is present. The tube is delivered in a compressed state and subsequently expanded via rotational motion. As it expands the outer surface of the tube contacts said plaque and forces it away from the centerline of the vessel thus increasing the vessel diameter. The device is then reconstrained to a smaller diameter and removed from the vessel. This procedure is generally referred to as angioplasty.

In another embodiment of the invention, an asymmetrically wrapped tube is configured to mechanically widen a lumen or cavity as described above but configured to then also be used to expand and/or hold said lumen of cavity to a desired diameter or shape, e.g., to function as a stent. Such a "hybrid" angioplasty and stenting device eliminates the need for separate devices and lessens treatment time.

In another embodiment of the invention, an asymmetric tube can be delivered in a constrained form to a site, for example an intravascular site, expanded via rotational, torsional force such that the outer surface of the device comes in contact with the vessel wall. Among other functions, the device may be configured to expand or hold open said vessel as described above (e.g., as a stent) or to deliver a substance to the vessel (e.g., a bioactive substance or therapeutic), said substance having been previously applied to the device. The device may then be reconstrained via rotational motion and removed from the site.

Figure 14A:
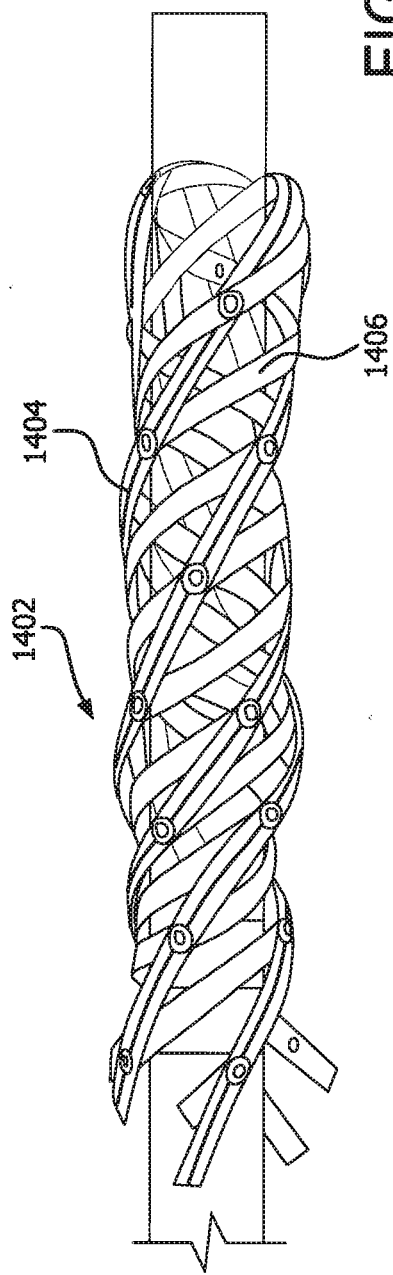
FIGS. 14A and 14B are elevation views of an expandable and contractible tubular device which is partially everted in a collapsed (A) and open (B) configuration.
Figure 14B:
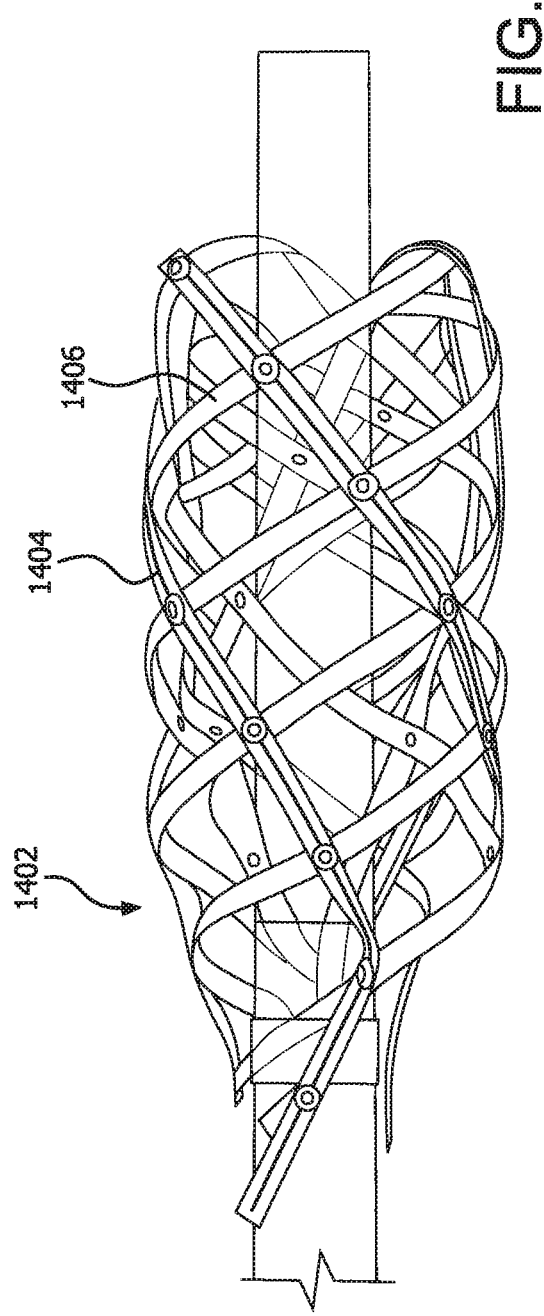

In another embodiment, the asymmetric design (as shown in FIG. 14B) can be constructed as a filter or retrieval basket. Tube 1306 depicted in FIG. 13B can be everted upon itself to make a retrieval device (e.g. a basket and/or funnel). FIG. 14A depicts a retrieval device 1402 in a collapsed configuration. FIG. 14B depicts the retrieval device in an open configuration 1402. Due to the asymmetric construction of filaments 1404 and 1406, the retrieval device and be collapsed and expanded via torquing. Thus, one embodiment of the invention comprises utilizing asymmetric biases construct to form a funnel or basket by rotating the affixed concentric tubes relative to one another. The funnel/basket can be constrained by rotating in the opposite direction. In one embodiment, said funnel/basket is an embolectomy filter. In another embodiment, said funnel/basket captures unwanted material in a vessel then collapses via torquing to capture said unwanted material. Alternatively, the basket structure may be retracted into a sheath to close it. Such applications are useful in medical conditions or procedures where emboli create a hazard to the patient and must be captured and removed, e.g., during clot disruption or arterial embolism due to conditions such as atrial fibrillation.

In a another embodiment, said open portion of the device, e.g., basket, may be advanced into a material or structure, for example a thrombus, tissue or previously placed construct (e.g., a medical stent or filter), held in place and reconstrained by rotational force thus cutting and/or retrieving and retaining the material or structure for subsequent removal. Such applications could include the taking of tissue and fluid biopsies, embolectomy, and the "snaring" and retrieval of medical devices. When combined with an aspiration function, the tube of the present invention also serves as an aspirator.

In another embodiment, the asymmetrically wrapped tubes of the invention may be configured as expandable members for deployment of other devices, much like inflatable balloons are currently used to expand and place medical stents, stent grafts or grafts. In this configuration, an asymmetrically wrapped tube would be positioned within an expandable device in at least a partially constrained state and then via rotational motion expanded to contact the expandable device and then further expanded to expand the expandable device. One advantage with this application is that during and after expansion any flow present proximate the expandable device will remain mostly uninterrupted, unlike the case with solid expandable members such as balloons. In another embodiment, the tube can be used to "seat" or touch up" the expansion profile of the stent or stent-graft.

In another embodiment, the asymmetrically wrapped tubes of the invention may be configured to restrict the extent to which an expandable device can expand. For example, rather than employing a cover on a balloon used to expand a stent or stent-graft to limit the diameter to which the balloon can expand, a tube of the present invention could be located over the balloon (or incorporated within the balloon material) and in accordance with the degree of rotational torsion applied to it expand to only a limited point thus limiting expansion of the balloon. Since the radial control offered by the tube is variable it could be used as a single product instead of the multiple products that are required today, each having their own maximum limiting diameter. Use as a constraining cover can also be applied to stent constraints. Thus, in one embodiment of the invention the tubular structure of is a constraining sheath.

In another embodiment, the asymmetrically wrapped tubes of the invention may be configured to variably release material or compounds located in association with said tubes. For example, in embodiments where said tubes are formed by filaments, the filaments can be dimensioned and laid tightly together in the constrained state of the device such that no openings of appreciable size exist between the filaments. In this state, the tube can be said to be at least relatively impermeable. Yet openings between filaments are created as the tube is torsionally expanded, thus increasing permeability. Because expansion can be tightly controlled, the size or area of the openings between the filaments can be similarly controlled and hence varied. Because the tube can be expanded and then re-constricted, the time during which the openings are present can be varied and/or repeated. One application of such a construct is as a bioactive material delivery device wherein an asymmetrically wrapped tube of the invention is placed to cover a bioactive material, e.g., a substrate over which has been coated a therapeutic either alone or complexed with a coating matrix like a polymer. The tube is constrained to at least mostly minimize the area of the openings present between the filaments. When placed at a desired location the tube can then be expanded by rotational motion to create openings between the filaments, increase permeability and allow the therapeutic material to pass external to the tube. Alternative substances may also be delivered in this fashion, e.g., polymers, sealants, dyes, liquids, gels, and the like. In addition, the construct described here could also be used to control the delivery of energy external to the tube, for example optical energy useful for photodynamic therapies. Subsequently, the tube could be removed from the delivery site or repositioned to another location. It should be noted that alternative embodiments are possible such as rather than using filaments to construct the tube that a construct as shown in FIG. 8 could be employed where slits 28 being closed when tube 10 is constrained would variably open as tube 10 is rotationally torqued. Permeability may also be controlled and optimized by using different dimension filaments in the tube.

In another embodiment, the asymmetrically wrapped tube of the invention may be used as a variable diameter delivery tube. For example, the tube may be configured as a variable diameter catheter, endoscope or introducer sheath which may be placed into the body at one diameter and subsequently expanded via the application of a torquing force. For example, peripherally inserted central venous catheters made in accordance with the invention may be percutaneously placed in a constricted (and thus smaller diameter) state then expanded to their working diameter. This helps avoid common complications of placing these relatively large catheters which include kinking or shearing at the clavicle and pinching-off the catheter as it passes between the first rib and the clavicle. Similarly, constructs made in accordance with the invention as introducer sheaths offer advantages over typical introducer sheaths. Typical sheaths are of set size and do not constrict in diameter as they are placed percutaneously. Thus the passage through skin, tissue and vessel(s) is of a diameter at least close to that of the introducer. Introducer sheaths made in accordance with the invention may be percutaneously placed at a much smaller diameter and then expanded with much less impact to surrounding tissues. An additional advantage of these medical constructs (such as central venous catheters and introducer sheaths configured in accordance with the invention) is that they are easily removed after being re-constricted by application of a rotational force.

In another embodiment, tubes of the invention may be configured as cannulatable grafts or shunts whereby a tube in its constructed state is configured to be more or less impervious to fluid passage but when expanded via torsional force the tube displays openings of varying size. A cannula or needle may be easily passed through said openings. When the needle is removed, the tube is re-constricted to close off the openings. This type of construct made in accordance with the invention may be used as a vascular access graft, commonly used for hemodialysis. A key advantage with such a construct is that the tube is not subject to repeated puncturing, wear and eventual failure as are typical access grafts.

In another embodiment, tubes of the invention may be configured to serve as electrodes where the tubes comprise conductive elements which are angularly displaceable, e.g., conductive wires. Alternatively the tube elements may be non-conductive, e.g., a high-dielectric polymer, but onto which are placed conductors. One embodiment of such devices is an ablation catheter which may be delivered at the reduced profile typical of a constrained embodiment of the invention and then expanded via rotational motion at the desired anatomical site. Such expansion may result in contact with tissue whereupon energy (e.g., RF energy) may be delivered through the catheter and the tube elements to the treatment site. Because the tube construct diameter may be readily varied the targeting and extent of ablation can be tightly controlled. In a similar embodiment, tubes of the invention could serve as implanted leads, e.g., for cardiac and neurological stimulation. Such constructs of the invention featuring conductive capabilities can also be used as sensors, e.g., to contact intracardiac tissue and transmit signals for electro-physiologic cardiac mapping.

Thus another embodiment of the invention is a temporarily-placed, rotationally expandable and contractible device which can be delivered, expanded, positioned and subsequently reconstrained and removed.

Another embodiment of the invention relies on the capacity of the asymmetrically wrapped tubes to expand and contract repeatedly upon application of opposing rotational forces. In one embodiment, the tubes are configured as hemostatic valves, typically found in catheter "hubs". When so configured, the tube is expanded to allow passage of a guidewire or elongate device, then constricted to seal the area around said guidewire or device from blood flow, then re-expanded when said guidewire or device needs to be removed from the catheter and "hub".

In another embodiment of the invention the asymmetrically wrapped tubes are configured to serve as external supports working to maintain an object's longitudinal position more or less stationary. For example a tube of the invention may be configured as a splint or cast which is placed over the body part (e.g., a broken arm) in an expanded state and then constricted to hold the part in a stationary longitudinal position, in the case of a broken arm for healing to occur. The tube is then easily removable by re-expanding its diameter through the application of a torsional force.

The translation of rotational force to angular displacement and thus radial expansion and contraction typical of constructs made in accordance with the invention make such devices useful in instances where radially compressive forces may be used to effect radial changes in such devices. For example, typical symmetrically-braided wire stents are commonly used in gastrointestinal applications like esophageal and gastroduodenal stents. These stents are subject to undesirable migration away from their deployment sites due to an "inch worming" effect caused by repeated radial compression. Such compression (e.g., that inherent to peristalsis) causes said stents to shrink axially then elongate. This repeated motion may cause the stent to move away from its placement site. This effect is especially pronounced when such radial compression occurs on one or the other end of a stent. In accordance with the invention, radial compression on asymmetrically wrapped tubes may reduce axial elongation sufficient to mitigate migration. This avoids the undesirable migration of devices like gastrointestinal stents. It will be understood that radial compression to effect rotational motion can be augmented by the direct application of an assistive, rotational force.

Devices made in accordance with the invention may feature an attachment to a delivery or positioning device such as a catheter, guidewire, rod or wire. Such attachments will vary but in cases where said devices must be located and/or deployed and then left in place, means are needed for detaching said devices from said delivery or positioning device. Such means are well known in the art.

Tubes made according to the invention can be made from a variety of materials. These materials comprise metals, such as nitinol, stainless steel, tantalum, titanium, tungsten, gold, platinum, iridium, rhodium and alloys thereof or pyrolytic carbon. Other materials comprise polymers such as polyurethane, high density polyethylene, polypropylene, and poly (dimethyl siloxane). Further still, the stents may be formed from biocompatible polymers that are bio-resorbable (e.g., bio-erodible or bio-degradable). Bio-resorbable materials are preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, hydroxy acids (i.e. lactide, glycolide, hydroxybutyrate), polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. Further still, the tubes may be formed of a polycarbonate material, such as, for example, tyrosine-derived polycarbonates, tyrosine-derived polyarylates, iodinated and/or brominated tyrosine-derived polycarbonates, iodinated brominated tyrosine-derived polyarylates polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. Additionally, the stent and/or tube could be comprised of any number of other polymers. In another embodiment, metals and polymers may be used to fabricate said tube in a composite, laminate reinforced material, or one that is simply coated with the material. Depending on desired characteristics, tubes may be constructed of materials with specific attributes. For example, in applications where the tube will be expanded and must remain so with little or no creep or re-constriction (that is it must "lock in place"), plastically deformable materials may be chosen for monolithic constructs. Conversely, should a tube need to remain compliant, meaning remaining capable of some degree of radial re-contraction and re-expansion, elastic materials may be chosen. It will be recognized that combining materials with different functional or behavioral attributes may be effected in selected instances. The configuration of the tubes of the invention may be varied to produce selected benefits. In one embodiment, the components making up the tube, e.g., filaments, are asymmetrically wrapped along the entire length of the tube. However, in other embodiments, asymmetrically-wrapped tubes can be interspersed and connected to torsionally-stable symmetrically-wrapped tube sections, the latter serving to transmit torque.

In one embodiment, said tube comprises any of the above mentioned materials formed by shaped materials such as filaments, tapes, wires or a combination thereof. In another embodiment, said tubular structure comprises a helically wrapped film. Said filaments, tapes, wires, film or combinations thereof are braided having an asymmetric bias as depicted in FIG. 13B, so that when the stent is contracted and expanded, the length is the final length and does not change and/or exhibit foreshortening.

There are additional uses for the invention which may extend into non-medical technical areas. These include expanding tubes or valves, e.g., to control pressure, couplers (where a constrained state of the tube couples two objects and releases them when expanded), clothing (e.g., jacket or pant leg cuffs), length controlled springs and anchors (where the tube would be inserted into a structure in its constrained state and then rotated to an expanded state and becomes anchored in the structure). Tubes of the invention may also be used as strain relief components.

Embodiments of the invention may be used as readily adjustable "locks" for adjustable systems. For example, a tube of the invention may be configured to work in association with a shock absorber. When contracted around the absorber, said absorber has less travel and visa versa when the tube is expanded.

It should be noted that the present invention may be scaled to virtually any dimension.

The forces required for the devices of the present invention to function in the desired fashion can be tailored to the application and rely upon several factors. These include geometry (in particular diameter), intrinsic strength of the elements, be they filaments or wrapped tapes, of the tubes, and how and where locations along the tubes are attached.

The torsional, torquing or rotational motion applied to the tubes of the invention may be generated to the tubes in various ways. In one embodiment, such force is applied manually. In other embodiments, said force may be generated mechanically (e.g., by motor and drive train), electromechanically (e.g., via electropolymers and the like), or hydraulically or pneumatically, among other means.

The torsional, torquing or rotational motion applied to the tubes may be transferred locally, that is one or both ends of the tube are manipulated directly. Alternatively, such force may be transferred over a distance. For example, one end of a tube may be attached to a guidewire within a catheter. When the guidewire is torqued, the rotational force is transferred to the tube end and the tube expands or contracts depending on the direction of rotation. Each method of force transfer has its advantages. In the latter case, for example, force transferred from a proximal end of a catheter to the distal end to effect expansion or contract could be used for stent placement, filter manipulation, expansion of an expandable device, and biopsy.

EXAMPLES

Without intending to limit the scope of the present invention, the following examples illustrate several embodiments of how the present invention may be practiced.

Example 1

Uniaxially Oriented ePTFE Film

This Example describes the assembly of an ePTFE tube that can be easily removed from an assembly mandrel. On a 0.136" steel mandrel a 1" wide expanded polytetrafluroethylene (ePTFE) film (having longitudinally oriented strength, minimal transverse and shear strength, and with FEP on one side functioning as an adhesive) was wrapped at 40° pitch relative to the mandrel axis in a right handed helix orientation with the FEP facing away from the mandrel. Next, a 0.25" wide ePTFE film was wrapped at a 74° pitch in a right handed helix orientation over of the first film with the FEP facing toward the mandrel. The assembly was then thermally processed on-mandrel at a temperature of 320° C. for 13 minutes. The tube was easily removed from the mandrel and no necking was observed at loads below material yield strength.

Example 2

Uniaxially Oriented ePTFE Film with Polyimide Film

This Example describes the assembly of an ePTFE tube comprising a non-compliant polyimide film (Kapton®) between the ePTFE layers. On a 0.236" steel mandrel a 1.0" wide ePTFE film was wrapped at a 56° pitch relative to the mandrel axis in a right handed helix orientation with the FEP facing away from the mandrel. Next, a 0.050"×0.001" polyimide film was wrapped at 82° pitch relative to the mandrel axis at a right handed helix orientation over of the first film. Then a 1" wide ePTFE film was wrapped at a 56° pitch relative to the mandrel axis at a right handed helix orientation on top of the polyimide film with the FEP facing toward the mandrel. The assembly was then thermally processed on-mandrel at a temperature of 320° C. for 13 minutes, after which tube was removed from the mandrel.

The non-compliant polyimide film used for high angle wrap limits axial strain and allows the use of a higher angle ePTFE wrap. The higher angle ePTFE wrap increases the "unwinding" effect for a given axial load. The diameter defined by polyimide wrap grows with axial tension but necking can be observed on the ePTFE between the polyimide.

Example 3

Uniaxially Oriented ePTFE Film with Polyimide Film

To see if the tube made in Example 2 can be modified to reduce necking, slits were created with a knife into the ePTFE in an orientation parallel that of the film structure (56° pitch relative to the mandrel axis), with approximately 0.050" spacing between the slits. These slits eliminate "off-axis" strength of ePTFE film allowing diametric growth of the polyimide helix under tension without ePTFE necking. Thus, the introduction of these slits eliminates necking.

Example 4

Uniaxially Oriented ePTFE Film

This Example describes the assembly of the ePTFE tube as described in Example 1 but on a scaled down version. On a 0.075" steel mandrel, a 0.25" wide ePTFE film was wrapped at a 25° pitch relative to the mandrel axis in a right handed helix orientation with the FEP facing away from the mandrel. Next, at 0.125" wide type ePTFE film wrapped at a 75° pitch relative to the mandrel axis in a right handed helix orientation with the FEP facing toward the mandrel. The assembly was then thermally processed on-mandrel at a temperature of 320° C. for 13 minutes. This construct was removed from the mandrel and was used as a device constraint which was everted for deployment.

Example 5

Uniaxially Oriented ePTFE Film with Polyimide Film

This Example describes the assembly of a tube which is nearly continuous polyimide which responds well to axial tension and returns to the starting diameter with little relative force. On a 0.083" steel mandrel, a 0.25" wide ePTFE film was wrapped at a 28° pitch angle relative to mandrel axis at a right handed helix orientation with the FEP facing away from the mandrel. Next, a 0.043"×0.001" polyimide film was wrapped at 68° pitch angle relative to mandrel axis in a right handed helix orientation over the first film. Then a 0.25" wide ePTFE film was wrapped at a 28° pitch angle relative to mandrel axis in a right handed helix orientation over the polyimide film with the FEP facing toward the mandrel. The assembly was then thermally processed on-mandrel at a temperature of 320° C. for 13 minutes.

Next, the tube was transferred to a 0.075" steel mandrel and the polyimide helix was "twisted down" or "coiled" to eliminate clearance between tube and mandrel, effectively increasing pitch angles for all the wraps. The tube was then compression wrapped with ePTFE film to immobilize it on the mandrel and thermally processed for 7 minutes at 320° C. after which the compression wrap was removed. The resultant tube is nearly continuous polyimide and responds well to axial tension, returning to the starting diameter with little relative force.

Example 6

Asymmetric Woven Nitinol Stent

This Example describes the construction of a self-expanding woven nitinol stent that can be torsionally constrained and subsequently deployed without a change in length. Nitinol wire, 0.007" nominal diameter, was braided in an opposing bias, over/under configuration to form a stent, as shown in FIG. 15A. A 6 mm diameter mandrel with pins projecting radially was used to facilitate weaving of the tubular wire form. The weave consisted of 8 wire strands in a helical orientation 1504 and 8 wire strands in an opposing helical orientation 1502. Strands 1502 were oriented at a pitch angle of about 54° relative to the axis while strands 1504 were oriented at a pitch angle of about 37° relative to the axis. The wire frame was thermally treated at 450° C. for ten minutes to set the shape. The stent was collapsed, as shown in FIG. 15B, by applying an angular displacement at one end of the tube relative to the opposing end, in a direction consistent with the larger pitch angle elements. The smaller pitch angle strands 1504 were reversed in direction and angularly displaced until they were approximately 37° relative to the axis in the same helical direction as the strands 1502 and length of the collapsed stent matches the length as woven. The stent is deployed by releasing the ends.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A tubular structure having a longitudinal axis comprising
    a first element oriented at a first angle of $\theta$ and a separate second element oriented at a second angle of $\gamma$, wherein:
    a. $\theta$ does not equal $\gamma$;
    b. $\theta$ and $\gamma$ are formed at an angle of between about +/−90 degrees relative to the axis of the tubular structure; and
    c. wherein when a first length section of the tubular structure is displaced rotationally relative to a second length section of the tubular structure, both $\theta$ and $\gamma$ change relative to the longitudinal axis and produce a change in diameter of at least a portion of the tubular structure, and wherein said tubular structure has a pre-expansion length that is the same as a post-expansion length.

2. The tubular structure of claim 1, wherein the angle of $\theta$ before expansion and angle of $\theta$ after expansion is equal.

3. The tubular structure of claim 1, wherein the angle of $\gamma$ before expansion and angle of $\gamma$ after expansion is equal and opposite in sign.

4. The tubular structure of claim 1, wherein said first and second elements comprise metal, polymer or a combination thereof.

5. The tubular structure of claim 1, wherein said tubular structure comprises a helically wrapped film.

6. The tubular structure of claim 5, wherein said tubular structure is a constraining sheath.

7. The tubular structure of claim 6, wherein said constraining sheath can be everted.

8. The tubular structure of claim 7, wherein as said constraining sheath is everted, the outer layer of the tube grows radially.

9. The tubular structure of claim 1, wherein said tubular structure is a stent.

10. The tubular structure of claim 9, wherein said stent further comprises a graft.

11. The tubular structure of claim 9, wherein said stent comprises stent rings.

12. The tubular structure of claim 1, wherein said tubular structure is a filter.

13. The tubular structure of claim 1, wherein at least a segment of the tubular structure has a given longitudinal stiffness, and wherein when a portion of the tubular structure is rotated so as to change $\theta$ and $\gamma$ relative to each other, the longitudinal stiffness of the at least a segment of the tubular structure changes.

14. The tubular of claim 1, wherein at least a segment of the tubular structure has a given length, and wherein when a portion of the tubular structure is rotated so as to change $\theta$ and $\gamma$ relative to each other, the length of the at least a segment of the tubular structure changes.

* * * * *